United States Patent
Davidson et al.

[11] Patent Number: 5,980,713
[45] Date of Patent: Nov. 9, 1999

[54] MICRO INJECTOR SAMPLE DELIVERY SYSTEM FOR CHARGED MOLECULES

[75] Inventors: James C. Davidson; Joseph W. Balch, both of Livermore, Calif.

[73] Assignee: The Regents of the University of California, Oakland, Calif.

[21] Appl. No.: 08/705,447

[22] Filed: Aug. 29, 1996

[51] Int. Cl.⁶ .......................... G01N 27/46; G01N 27/447
[52] U.S. Cl. .......................... 204/456; 204/466; 204/606; 204/616
[58] Field of Search ..................... 204/600, 606, 204/607, 608, 609, 610, 612, 613, 614, 615, 616, 617, 618, 619, 620, 621, 450, 456, 457, 458, 459, 461, 462, 463, 464, 465, 466, 467, 468, 469, 470, 284, 280

[56] References Cited

U.S. PATENT DOCUMENTS

| | | | |
|---|---|---|---|
| 4,270,986 | 6/1981 | Smith | 205/206 |
| 4,301,794 | 11/1981 | Tapper | 604/20 |
| 4,406,658 | 9/1983 | Lattin et al. | 604/20 |
| 5,002,527 | 3/1991 | Reller et al. | 604/20 |
| 5,088,977 | 2/1992 | Sibalis | 604/20 |

FOREIGN PATENT DOCUMENTS

| | | | |
|---|---|---|---|
| 4319728 | 12/1993 | Germany | 204/606 |
| 63-85347 | 4/1988 | Japan | 204/606 |
| 63-85348 | 4/1988 | Japan | 204/616 |
| WO94/11529 | 5/1994 | WIPO . | |

*Primary Examiner*—Robert Warden
*Assistant Examiner*—John S. Starsiak, Jr.
*Attorney, Agent, or Firm*—L. E. Carnahan

[57] ABSTRACT

A micro injector sample delivery system for charged molecules. The injector is used for collecting and delivering controlled amounts of charged molecule samples for subsequent analysis. The injector delivery system can be scaled to large numbers (>96) for sample delivery to massively parallel high throughput analysis systems. The essence of the injector system is an electric field controllable loading tip including a section of porous material. By applying the appropriate polarity bias potential to the injector tip, charged molecules will migrate into porous material, and by reversing the polarity bias potential the molecules are ejected or forced away from the tip. The invention has application for uptake of charged biological molecules (e.g. proteins, nucleic acids, polymers, etc.) for delivery to analytical systems, and can be used in automated sample delivery systems.

17 Claims, 2 Drawing Sheets

MICRO INJECTOR SAMPLE DELIVERY SYSTEM FOR CHARGED MOLECULES

The United States Government has rights in this invention pursuant to Contract No. W-7405-ENG-48 between the United States Department of Energy and the University of California for the operation of Lawrence Livermore National Laboratory.

BACKGROUND OF THE INVENTION

The present invention relates to molecular analysis systems, particularly to high throughput analysis systems, and more particularly to a micro injector sample delivery system for charged molecules involving an electric field controllable loading tip.

Most clinical, molecular, or forensic projects involve the characterization of DNA fragments or molecules by one or more methods. In efforts to speed up such characterization, high throughput analysis systems are being developed.

High throughput analysis systems depend on high densities of analysis channels/lanes. Manual introduction of samples becomes a limiting factor when more than 24 to 36 samples are being transferred. This is due to sample diffusion over time, operator fatigue and inability to precisely load high density channels/lanes which are micrometers wide as opposed to millimeters. Thus, there is a need in the art for an automated system for the introduction of samples for analysis.

The present invention satisfies that need by a micro injector system for collecting and delivering controlled amounts of charged molecule samples for subsequent analysis. The essence of the micro injector system is an electric field controllable loading tip which includes porous material and enables the migration of charged molecules toward or the forcing of the molecules away from the porous material, by interchanging the polarity of the potential bias on the loading tip.

SUMMARY OF THE INVENTION

It is an object of the present invention to provide means for increasing the throughput of charged molecule samples in an analysis system.

A further object of the invention is to provide a micro injector sample delivery system for charged molecules.

A further object of the invention is to provide a device for collecting and delivering controlled amounts of charged molecule samples for subsequent analysis.

A further object of the invention is to provide a method for sample and effective collection and delivery of charged samples.

Another object of the invention is to provide a micro injector charged molecule sample delivery system which can be scaled to large numbers for sample delivery to massively parallel high throughput analysis system.

Another object of the invention is to provide a method involving changing of polarity bias potential on a micro injector enables collection and delivery of charged sample to an analysis system.

Another object of the invention is to provide a micro injector sample delivery system for charged particles which utilizes an electric field controllable loading tip.

Another object of the invention is to provide a loading tip for a charged particle sample delivery system which utilizes a change in polarity of the potential bias thereon for collecting and delivering charged molecules.

Other objects and advantages of the present invention will become apparent from the following description and accompanying drawings. The invention involves a micro injector sample delivery system for charged molecules which utilizes an electric field controllable loading tip. The loading tip is made of conducting material and includes a quantity of porous material which functions to collect the sample and then deposit it onto analysis channels. This is accomplished by changing the polarity of the potential bias on the tip. The micro injector system can be scaled to large numbers (>96) for sample delivery to massively parallel high throughput analysis systems. The invention can be utilized for the uptake of charged biological molecules (e.g. proteins, nucleic acids, polymers, etc.) for delivery to analytical systems. Also, the invention has application in automated sample delivery systems for biomolecular analysis, such as DNA analysis systems based on electrophoresis.

BRIEF DESCRIPTION OF THE DRAWINGS

The accompanying drawings, which are incorporated into and form a part of the disclosure, illustrate embodiments of the invention and, together with the description, serve to explain the principles of the invention.

DETAILED DESCRIPTION OF THE INVENTION

The invention involves a device which is used for collecting and delivering controlled amounts of charged molecule samples for subsequent analysis. The micro injector sample delivery system for charged molecules can be scaled to large numbers (>96) for example delivery to massively parallel high throughput analysis systems. The collection and delivery system of the present invention can be utilized, for example, in automated DNA analysis systems based on electrophoresis, or other system involving the uptake of charged biological molecules for delivery to analytical systems.

High throughput analysis systems depend on high densities of analysis channels/lanes. The present invention enables introduction of samples in such high throughput analysis systems by a micro injector arrangement utilizing electric field controllable loading tips which collect or deliver the sample based on the polarity bias potential to the micro injector tip relative to the sample well and the analysis channel. Thus, the micro injector system of this invention provides the ability to precisely load high density parallel high throughput analysis systems using channel/lanes which are micrometers wide.

The essence of this invention is the use of electric field controllable micro injector loading tips. Each tip is made of a conducting material, such as metal or silicon, which can be micromachined with a notched pocket for retaining a small amount of porous material (e.g. agaraose, fritted glass, Teflon, or other porous plastics) which will collect the sample prior to electroinjection onto an analysis channel or lane. The micro injector is operated by submerging the tip in a microtiter plate sample well and applying an appropriate polarity bias potential (e.g. a positive bias potential for negative charged molecules such as DNA and proteins) to the micro injector tip relative to the sample well. This will allow the charged molecule to migrate into the porous medium at the end of the tip. The tip is then withdrawn from the microtiter plate well and placed at the inlet of an analysis channel. The polarity of the potential bias is reversed and applied to the micro injector relative to the analysis medium thus ejecting or forcing the charged molecules away from the porous material in the tip and into the channel medium for subsequent analysis.

Figure 1:
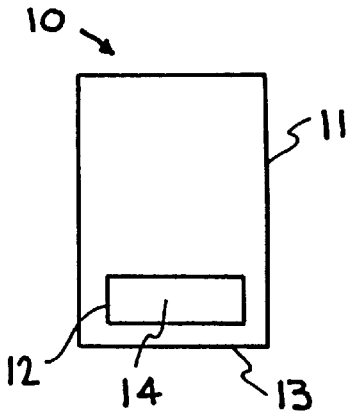
FIG. 1 illustrates an embodiment of a single micro injector tip made in accordance with the invention.

Referring now to the drawings, FIG. 1 illustrates an embodiment of a micro injector generally indicated at 10 and composed of a body or conducting electrode 11 having a notched section 12 at one end or tip 13 which contains porous medium or material 14. The conducting electrode or body 11 may be composed of silicon, aluminum, platinum and conducting polymers or metal coated ceramics, glasses or plastics, or any electrically conductive material. The porous material 14 may be agaraose, fritted glass, non-doped porous silicon, polymers such as polyacrylamide, or porous plastics such as Teflon (polytetrafluoroethylene), nylon, or cellulose. By way of example the electrode 11 may have a length of 0.5 to 2.0 cm, width of 1 to 5 mm and thickness of 1 mm, with the notched section 12 having a width of 1 to 3 mm, height of 50 to 100 $\mu$m, and depth of 50 to 200 $\mu$m.

Figure 2:
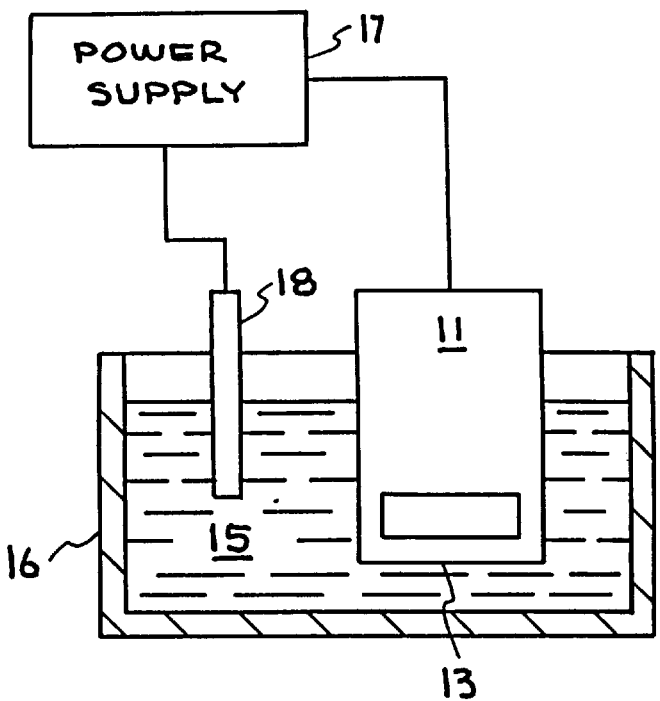
FIGS. 2 and 3 illustrate the operation of the tip for collecting and delivering negatively charged molecules such as DNA.

FIG. 2 illustrates loading the micro injector 10 with, for example, a DNA sample or molecule 15 from a microtiter plate sample well 16. This is accomplished by connecting a power supply 17 between the micro injector 10 and the microtiter plate sample well 16. Since DNA sample or molecule 15 is generally negatively charged, the power supply 17, having polarity reversing means, 17', is electrically connected such that the polarity bias potential is positive with respect to the electrode 11 of micro injector 10 and negative with respect to an electrode 18 on the sample well 16, as illustrated in FIG. 2. This causes a negatively charged DNA sample or molecule 15 to migrate into the porous medium or material 14 on the tip 13 of micro injector 10. The micro injector 10 is then withdrawn from the microtiter plate sample well 16 and transferred to an analysis channel, as illustrated and described hereinafter with respect to FIG. 3.

Figure 3:
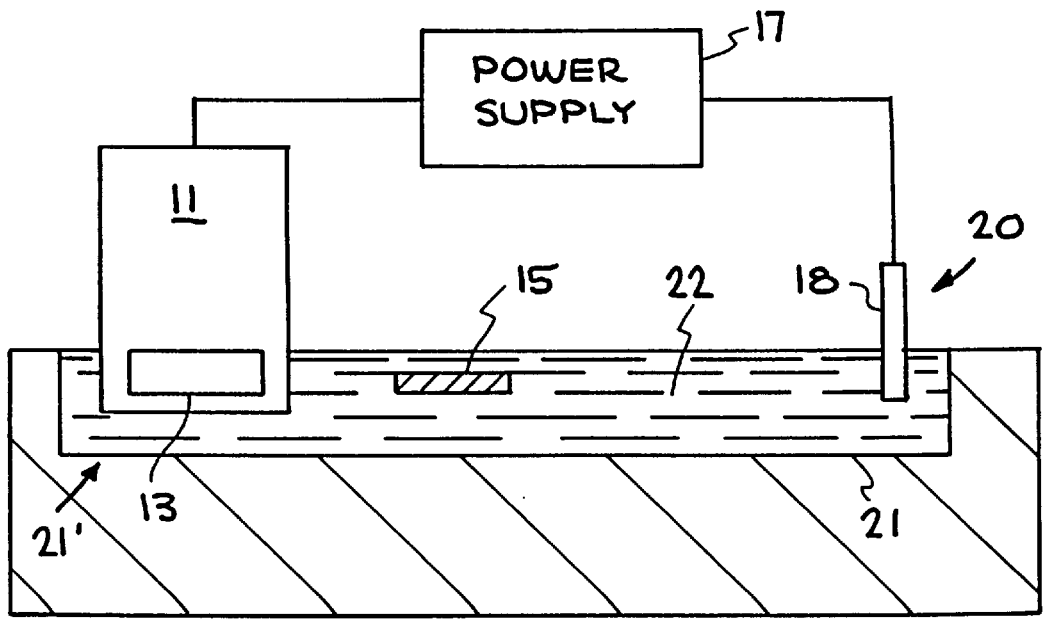

FIG. 3 illustrates injection of DNA sample 15 from the micro injector 10 into an analysis system generally indicated at 20. The analysis system 20 includes a number of channels 21, only one shown, containing an appropriate medium or solution 22, such as hydroxy ethylcellulose, linear polyacrylamide, or polyethylene glycol. The channel 21, for example, may be made from glass, ceramics, high resistance silicon, or other electrically insulating substrate, and have a width of 10 to 1000 $\mu$m and depth of 10–200 $\mu$m. With the tip 13 of electrode 11 withdrawn from sample well 16, it is placed at an inlet of channel 21, as shown in FIG. 3, with the electrode 18 in contact with medium or solution 22. The polarity of the potential bias produced by power source 17 is reversed (negative to electrode 11, positive to electrode 18) and applied to the micro injector electrode 11 relative to the analysis medium 22 thus ejecting or forcing the negatively charged DNA sample or molecule 15 away from the porous material 14 in tip 13 and into the channel medium 22 for subsequent analysis. Devices for reversing the polarity of a power source are well known. The micro injector 10 is then returned to the microtiter plate sample well to load another sample or molecule. While not shown, the power supply 17 can be connected to both the sample well and the channel.

Figure 4:
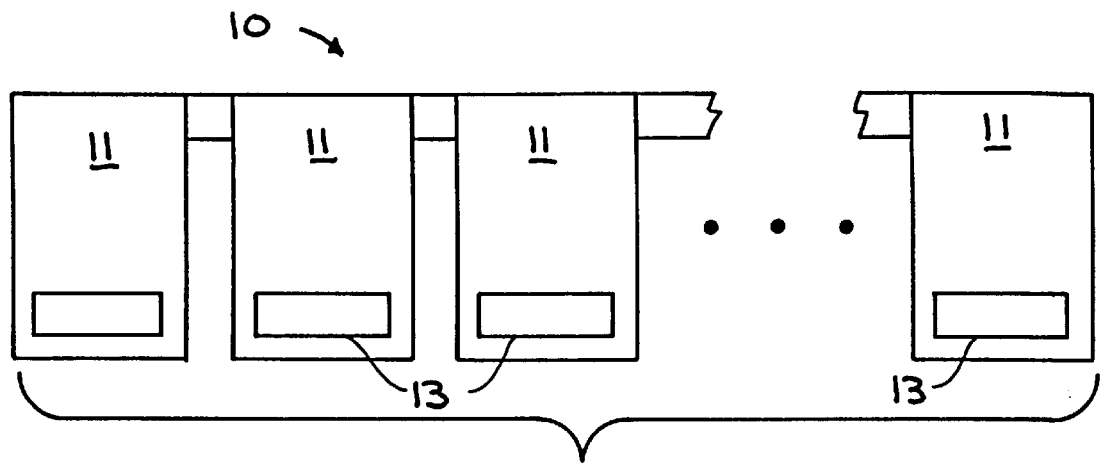
FIG. 4 illustrates a linear array of tips similar to the micro injector tip of FIG. 1.

FIG. 4 illustrates a linear array of micro injectors 10 having tips 13 constructed as described above in FIG. 1. The array is composed of any desired number (1–n) of micro injectors, and for example n may equal 8 or 12 micro injectors 10 in each row, depending on the design of the analysis system to be utilized therewith. In operation the micro injectors of the FIG. 4 array may be electrically connected to the same power supply, or different injectors may be connected to different power supplies such that either negatively or positively charged samples or molecules can be loaded into the tip via the porous material therein.

Figure 5:
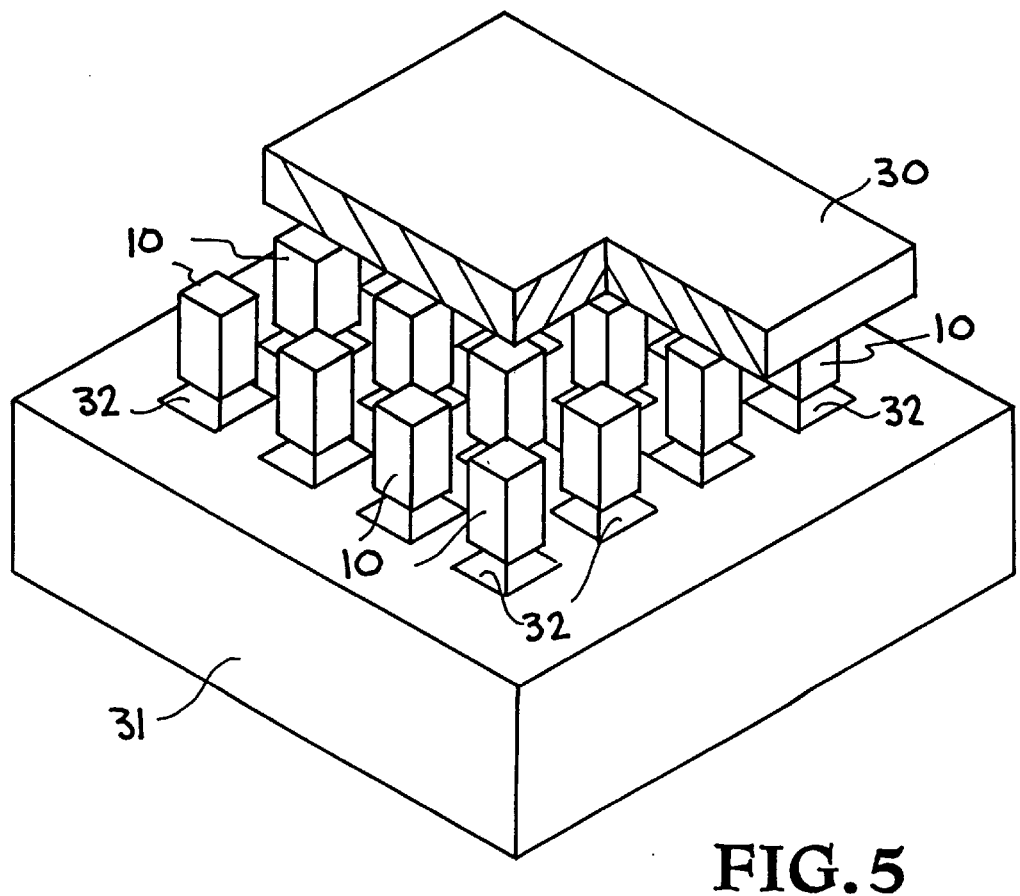
FIG. 5 illustrates a 2-D tip array which matches a microliter plate and channel array input format.

FIG. 5 illustrates in two-dimensions a tip array 30 and containing numerous micro injectors 10 (a) matching microtiter plate 31 having numerous sample wells 32, whereby the tip array 30 can simultaneously load samples or molecules from the corresponding sample wells 32, be the samples positively or negatively charged, by applying the appropriate polarity bias potential between the electrodes of the individual tips and sample wells, as described above with respect to FIG. 2. After loading of the desired samples, the array 30 is moved to an analysis system having channels which cooperate with the micro injector configuration of the array 30. By reversing the polarity of each of the micro injectors of array 30, the samples are injected into the channels of the analysis system as in FIG. 3. Thus, if for example, each of the micro injectors of array 30 have the same polarity bias, samples can be quickly loaded from the microtiter plate and transferred to the analysis system, thus expediting analysis of the samples.

It has thus been shown that the present invention provides a simple yet effective device for collecting and delivering controlled amounts of charged molecule samples for subsequent analysis. It has also been shown that the micro injector of the invention can be scaled to large numbers to enable expedition of sample analysis. The micro injector is of a simple constructed and requires only a reversible polarity power supply to enable collection and delivery of charged samples.

While particular embodiments, materials, parameters, etc. have been illustrated and/or described to exemplify and explain the principles of the invention, such are not intended to be limiting. Modifications and changes may become apparent to those skilled in the art, and it is intended that the invention be limited only by the scope of the appended claims.

The invention claimed is:

1. In a system for collecting charged samples and delivering same for analysis, including a plurality of electrodes and means for creating a potential between the electrodes, the improvement comprising:

one of said electrodes being constructed to be positioned in a sample well containing a sample to be delivered or positioned in an analysis channel medium into which a sample is to be delivered;

another of said electrodes comprising a conducting electrode;

said conducting electrode including a quantity of porous material at one end thereof; and means for reversing polarity of a bias potential applied to at least said conducting electrode.

2. The improvement of claim 1, wherein said quantity of porous material is retained in a notch in said conducting electrode.

3. The improvement of claim 1, wherein said conducting electrode is composed of material selected from the group consisting of silicon, aluminum, platinum, conducting polymers, and metal coated ceramics, glasses, and plastics.

4. The improvement of claim 1, wherein said porous material is composed of material selected from the group consisting of agaraose, fritted glass, non-doped porous silicon, polymers including polyacrylamide, and porous plastics selected from polytetrafluoroethylene, nylon, and cellulose.

5. The system of claim 1, wherein said means for creating a potential between the electrodes comprises a power supply operatively connected to said conducting electrode and to said one electrode.

6. A micro injector sample delivery system for charged molecules, comprising:
- at least one micro injector;
- a microtiter plate having at least one sample well containing a charged molecule to be delivered;
- an analysis system having at least one channel into which a charged molecule is to be delivered;
- said at least one micro injector including a tip containing a porous material; and
- means for applying an appropriate polarity bias potential on said at least one micro injector and one of said sample well and said channel;
- whereby a charged molecule is collected by said micro injector upon a certain bias potential being applied to said micro injector and to said sample well, and is discharged from said micro injector upon said bias potential applied to said micro injector and to said channel being reversed.

7. The system of claim 6, wherein said tip of said micro injector includes a notch having a quantity of porous medium therein.

8. The system of claim 7, wherein said porous medium is selected from the group consisting of agaraose, fritted glass, non-doped porous silicon, polymers including polyacrylamide, and porous plastics selected from polytetrafluoroethylene, nylon and cellulose.

9. The system of claim 6, wherein said micro injector includes a conducting electrode.

10. The system of claim 9, wherein said conducting electrode is composed of material selected from the group consisting of silicon, aluminum, platinum, conducting polymers, and metal coated ceramics, glasses and plastics.

11. The system of claim 9, wherein said conducting electrode includes a tip having a notch therein, said notch containing porous material.

12. The system of claim 11, wherein said porous material is selected from the group consisting of agaraose, fritted glass, non-doped porous silicon, polymers including polyacrylamide, and porous plastics selected from polytetrafluoroethylene, nylon, and cellulose.

13. The system of claim 6, comprising an array of said micro injectors, said microtiter plate having a plurality of sample wells adapted to align with said array of micro injectors, said analysis system having a plurality of channels adapted to align with said array of micro injectors.

14. A method for collecting and delivering at least one charged molecule, comprising:
- providing at least one micro injector having a tip containing a porous material;
- providing at least one sample well containing at least one charged molecule;
- providing an analysis system having at least one channel therein;
- positioning at least the tip of the micro injector in the sample well;
- applying a potential to the micro injector and the sample well thereby causing the charged molecule to migrate into the porous material; and
- applying a potential to the micro injector and to the channel such that the polarity on the micro injector is the same as the polarity of the charged molecule, thereby causing the charged molecule to be ejected from the porous material into the channel of the analysis system.

15. The method of claim 14, additionally including electrically connecting the micro injector to the sample well, and repeating of collecting and delivery operations.

16. The method of claim 14, wherein providing the at least one micro injector is carried out by:
- forming at least a section of the at least one micro injector from an electrically conducting material to define an electrode;
- forming a notch in one end of the electrode defining the tip; and
- providing a porous material in the notch of the electrode.

17. The method of claim 14, additionally including:
- providing an array of micro injectors;
- providing a plurality of sample wells containing charged molecules;
- providing the analysis system with a plurality of channels; and
- collecting charged molecules from the sample micro injectors onto the channels of the analysis system.

* * * * *